United States Patent [19]
Hansske et al.

[11] Patent Number: 5,907,047
[45] Date of Patent: May 25, 1999

[54] PAPYRACILLIC ACID, METHOD FOR PREPARATION AND ITS USE AS SYNTHON FOR BIOACTIVE SUBSTANCES

[75] Inventors: Fritz Hansske, Hirschberg, Germany; Olov Sterner, Malmö, Sweden; Marc Satadler, Stelzenberg, Germany; Heidrun Anke, Kaiserslautern, Germany; Liesel Dörge, Am Schelmenbuckel, Germany; Rudong Shan, Lund, Sweden

[73] Assignee: Boehringer Mannheim GmbH, Mannheim, Germany

[21] Appl. No.: 09/051,920

[22] Filed: Jul. 23, 1998

[30] Foreign Application Priority Data

Oct. 27, 1995 [EP] European Pat. Off. ............... 95116932
Sep. 14, 1996 [EP] European Pat. Off. ............... 96114768

[51] Int. Cl.$^6$ ................................. A61K 31/37; C07D 493/10
[52] U.S. Cl. ............................. 549/265; 435/118; 436/501; 514/299; 514/462; 546/112; 562/577
[58] Field of Search ............................. 549/265; 546/112; 562/577; 514/299, 462

[56] References Cited

PUBLICATIONS

Black, J. Chem. Soc., C, No. 12, pp. 1123–1127, 1966.

*Primary Examiner*—Bernard Dentz
*Attorney, Agent, or Firm*—Nikaido, Marmelstein, Murray & Oram LLP

[57] ABSTRACT

This invention relates to a new biologically active compound as shown in formula (I) and its biologically active derivatives; whereas derivatives are produced by the reaction of formula (I) with nucleophiles.

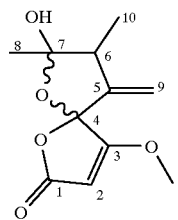

23 Claims, No Drawings

PAPYRACILLIC ACID, METHOD FOR PREPARATION AND ITS USE AS SYNTHON FOR BIOACTIVE SUBSTANCES

This application is a 371 of PCT/EP96/043636 filed Oct. 25, 1996.

DESCRIPTION

This invention relates to a new biological active compound (I)

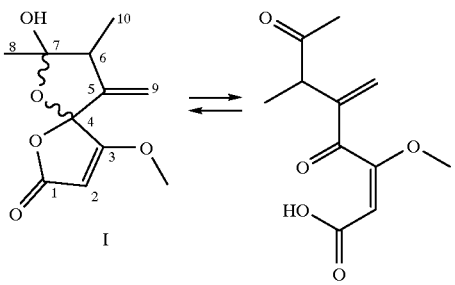

The compound called papyracillic acid can be in an equilibrium of its open chain form.

Due to its reactivity, compound (1) can be used as an educt for a wide range of new compounds. Possible derivatives of papyracillic acid are such where the hydrogen of the hydroxy group of C-7 is substituted by a branched or an unbranched $C_1$–$C_4$-Alkylether.

Another possibility of derivatization of compound (I) is the reaction of (I) with different nucleophiles Y. The potency of (I) as an electrophile can be demonstrated by the reaction of (I) with the nucleophile cysteine or cysteine methyl ester. Both yield in essentially one respective product which is surprisingly formed by nucleophic binding at C-9. The reaction between (I) and $Ac_2O$ in pyridin yields inter alia in a compound where Y symbolizes OAc.

An introduction of an additional ring system into papyracillic structure can be demonstrated by the reaction of (I) with Trimethylsilyldiazomethane ($TMSCHN_2$). The reaction of (I) with $TMSCHN_2$ yields inter alia to products of 1–3 dipolar cycloaddition. Again, the carbon on position C-9 of (I) is electrophilic. C-9 and C-5 of (I) are members of the introduced ring system in papyracillic acid. An unexpected number of products was obtained under the acetylation conditions in pyridine and by the reaction of papycillic acid with glycine. Both reactions are illustrative examples that papyracillic acid can in addition be used as reactive electrophilic educt to create a diversity of products.

This diversity of products can be used directly or after one or more separation steps as plurality of compounds like chemical libraries for the search of active principles as lead structures in drug discovery for further optimization. From such pluralities of compounds the active principle can be obtained by separation from the mixture. Such an active principle cannot only serve as lead structure but can be a pharmacophor or compound useful for plant protection by itself. Another aspect of the invention concerns the preparation of plurality of compounds by reacting papracillic acid with different reactive compounds, preferrable nuclephiles (which may be for example different heterocycles or with different amino acids).

A method of determining whether a compound plurality or its subsets interact with a target of interest comprises
  a) providing a target of interest
  b) incubating said target with said compound or compound plurality
  c) determining whether said target exhibits a responsive change.

Is such a compound selected for further lead structure optimization or pharmacophor identification as an additional step d), the variation of the structure of said compound can be performed. During the lead structure optimization and pharmacophor identification the variation of the structure can be done by conventional chemical means or molecular modelling. The same is true for steps a) to c) of the above-mentioned method which can be done by traditional biological/biochemical means or also by molecular modelling.

Targets of interest are for example pharmaceutical or plant protection targets. Those targets include proteins (receptors, ion channels, signal transduction proteins, enzymes etc.), cells, parts of cells, DNA, RNA etc. Whether a compound or compound plurality shows a responsive change with the target of interest can be detected by, for example, colour reaction activation or inactivation of reactions etc.

More particularly, this invention relates to papyracillic acid (I), derivatives and salts thereof especially their pharmaceutical acceptable salts, to process of preparation thereof and to bioactive, preferred pharmaceutical, compositions comprising the same. Further derivatives of papyracillic acid are obtained by reaction of (I) with alkylation agents.

Prodrugs of papyracillic acid and its derivatives are included in this invention. For isolation and purification, pharmaceutical unacceptable salts can be used as well.

The compound (I) and its derivatives can be solvated, especially hydrated. Hydration may happen during preparation or storage.

Compound I and its derivatives show different asymmetric centres. The invention includes racemates and optically active forms of papyracillic acid.

In addition it was found that papyracillic acid shows antibiotic activity.

The invention includes fermentation fluids, extracts, and concentrated solutions which contain papyracillic acid or its derivatives.

Papyracillic acid can be produced by culturing a papyracillic acid producing strain, e.g. Ascomycete *Lachnum papyraceum* (Karst.) Karst. in a nutrient medium containing $CaBr_2$.

A related compound is Penicillic acid which is a classical mycotoxin produced by various fungi including the genera Penicillium and Aspergillus. Together with patulin, isopatulin and ascladiol it constitutes a class of chemically relatively simple 5-membered cyclic lactones, which due to their toxicity and carcinogenicity are considered to be a potential health hazard to animals and man. [R. J. Cole, R. H. Cox, Handbook of Toxic Fungal Metabolites, p. 510–526, Acadamic Press, New York, 1981].

Penicillic acid (II) can be used to create a multitude of libaries in a very similar manner as papyracillic acid. In the case of penicillic acid the reactive carbon for nucleophilic binding is C-6..

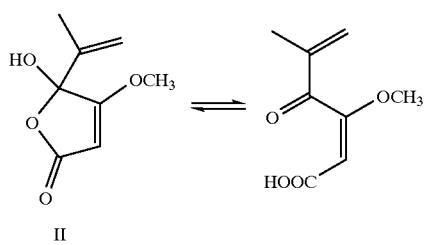

II

The micro-organism which can be used for the production of papyracillic acid is a papyracillic acid producing strain belonging to the genus Ascomycetes. Morphological, biological, physiological and cultural characteristics of Ascomycetes Lachnum papyraceum can be found in [Dennis, R. W. G. A revision of British Hyaloscyphaceae with notes on related European species. Mycol. Papers 32 Kew 1949; Karsten, P. A.; Mycologia Femica. Parsprima. Discomycetes Bildrag till Kannedom of Finnlands Natural Folk, Helsingtors, pp. 1–263, 1871]. Synonyms used for Lachnum papyraceum are: Lachnum (syn. Dasyscyphella, Dasyscyphus, Dasyscypha) papyraceum (syn. papyraceus) (Karst.) P. Karst. [Ainsworth, G. C., Sparrow, F. K. & Sussman, A. S. (eds.) The fungi. An advanced treatise. Vol IV A: A taxonomic review with keys: Ascomycetes and Fungi Imperfecti. Academic Press New York/London (1976), p. 297].

Ascomycetes Lachnum papyraceum, strain 48–88, was collected in 1988 in Hinterstein, Germany. A voucher specimen, which showed the characteristics of the genus and species according to Dennis and Karsten, and strain A 48–88 (obtained from the ascospores) are deposited in the herbarium and the culture collection of the Lehrbereich Biotechnology, University of Kaiserslautern. It is deposited as well with DSM, Deutsche Sammlung von Mikroorganismen und Zellkulturen GmbH, Mascheroder Weg 1b, D-38124 Braunschweig, Germany, under accession number DSM 10201 (the deposition date is Aug. 3, 1995).

It is to be understood that the production of papyracillic acid is not limited to the use of the particular organism described herein, which is given for the illustrative purpose only. This invention also includes the use of any mutants which are capable of producing papyracillic acid including natural mutants as well as artificial mutants which can be produced from the described organism by conventional means such as irradiation of X-ray, ultra-violet radiation, treatment with N-methyl-N'-nitro-N-nitrosoguanidine, 2-aminopurine, and the like.

For growth of Ascomycetes Lachnum papyraceum and therefore production of papyracillic acid, all suitable culturing methods can be used resulting in production of sufficient bio mass. In general, seeding of Ascomycetes Lachnum papyraceum and fermentation to papyracillic acid is independent of used container, fermentors and starter proceedings.

Fermentation of the fungus was sucessful in MGP medium [Example 1, Lit. Stadler et al. J. Antibiotics 48, 149–154, 1995] with 100 mM calcium bromide, but other culture media like BAF medium [Singer, R. The Agaricales in modern taxonomy. Springer Verlag Berlin/Heidelberg/New York 1976), YMG media (glucose 0,4% or 1% respectively; malt extract 1,0%, yeast extract 0,4%, and malt extract medium (malt extract 0,5–5%) were also suitable for the production of papyracillic acid. The production of compounds I was also observed in Potato Dextrose broth, CMG broth, Czapek-Dox broth (with glucose or sucrose respectively) and cornmeal medium (if not specified otherwise, these culture media are described in the ATCC Media Handbook, American Type Culture Collection Rockville, Md., USA 1984).

Assays for antibiotic activity of the extracts of fermentations to which 100 mM $CaBr_2$ was added at the onset of the secondary metabolism indicated that strongly active metabolites are formed during these conditions, and TLC analyses show that a new product that has not been observed during previous fermentations of the fungus is formed in large amounts. The new product (I) was obtained by silica gel chromatography, and spectroscopic characterisation by NMR suggested that it is a mixture of four isomers (approximately 1:1:2:4 in chloroform according to the $^1$H NMR spectrum).

Preferred fermentation conditions and media are given in example 1.

Derivatives of papyracillic acid

Derivatives of papyracillic acid, where C-7 of I is substituted by OR instead of OH with R equals $C_1$–$C_4$-Alkyl are included in this invention.

These compounds can be generally obtained by reaction of compound (I) under appropriate conditions (e.g. example 3).

The methylation of papyracillic acid (I) with Trimethylsilydiazomethane ($TMSCHN_2$) in Benzene/Methanol 1:1 yielded an unexpected number of products (cf. Example 4–6).

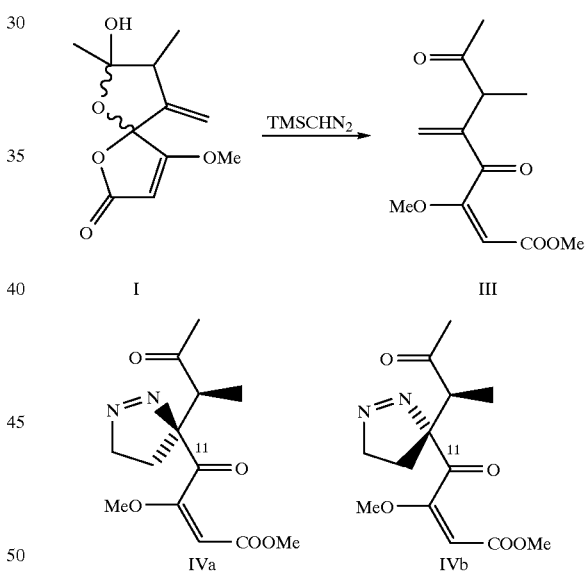

The methyl ester III is formed rapidly, and is the major product as long as reaction time is short (minutes). In addition, the two azo derivatives (IVa) and (IVb) were formed together with the ester (III). The formation of similar cyclic azo products (via a 1,3-dipolar cycloaddition of the reagent to the double bond) when α,β-unsaturated carbonyl compounds are treated with diazomethane or TMS-diazomethane has been reported, although these normally are oxidised to pyrazoles or rearranged to pyrazolines. [Aoyama, T.; Iwamoto, Y.; Nishigaki, S.; Shiori, T. Chem. Pharm. Bull. 1989, 37 253–256].

Papyrallic acid (I) can be used for synthesizing a huge number of different compound pluralities by reaction of (1) with different nucleophiles Y. Compound pluralities consisting either of reaction products of (1) with a single nucleophile $Y_1$ or a number of different nucleophiles $Y_1, Y_2 \ldots Y_n$ can be used for screening of new drugs or lead structures for drugs in different assays. In the case of desired results (e.g. activation or inhibition of a reaction of interest in a receptor or cell assay), sets of compound pluralities can be constructed. Such subsets are either produced by reducing the number of nucleophiles reacting or by separation of groups of products from the compound plurality by conventional means like chromatography, solvent extraction etc. If, for example, the multitude of individual products reduce the effective amount for the single product to a concentration to low for meaningful assaying either pure substances or subsets of substances can be used for assaying. Pure substances are obtained by conventional purification technology. Interesting compound libraries are produced by the reaction of a nucleophile Y with the electrophilic C-9 of (I). Examples of nucleophiles are amines, alcohols and thiols all of aliphatic or aromatic hydrocarbons which may be substituted by themselves. Aliphatic hydrocarbons are, for example, saturated or unsaturated, branched or unbranched aliphatic groups containing 1–20 carbon atoms. Aromatic hydrocarbons are, for example, monocyclic rings having 5–7 members or bicyclic rings having 8–12 members. Other examples of nucleophiles are substituted or unsubstituted heterocycles. Examples of heterocycles are monocyclic rings having 5–7 members with 1–3 heteroatoms each independently selected from N, S and O, or bicyclic rings having 8–12 members with 1–5 heteroatoms each independently selected from N, S and O. Such are for example pyridine, pyridazine, pyrimidine, pyrazine, thiazols, oxazols, imidazols, purins, chinolins, benzochinolins etc. In a similar way compound pluralities with penicillic acid (II) as electrophile are synthesized.

An example of a single library with (I) is shown in the following scheme.

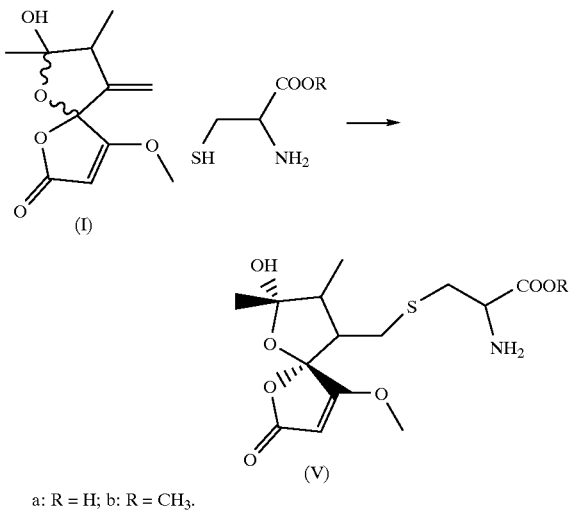

a: R = H; b: R = CH$_3$.

The reaction between papyracillic acid (I) and cysteine and its methyl ester was fast and yielded essentially one respective product. No attack on C-3 of papyracillic acid (I) was observed. The structures of the adducts (Va) and (Vb) were determined by the HMBC correlations observed between 9-H$_2$ and C-11, as well as between 11-H$_2$ and C-9, and the NOESY correlations between 6-H and 5-H as well as 8-H$_3$, between 9-H$_2$ and 10-H$_3$, and between 3-OCH$_3$ and 5-H. In the case of reaction with Glycin a huge number of products is obtained.

To illustrate the plurality of reactions which papyracillic acid (I) is able to undergo, (I) was acetylated in pyridine and it was observed that several products are formed. The major product was found to be compound (VI) which together with compound (VIIa) may be formed by the addition of acetate to the electrophilic papyracillic acid (I). In addition, and unexpectedly, the three indolizine derivatives (VIII), (IX) and (X) were obtained, apparently formed after the nucleophilic attack by pyridine. The NMR chemical shifts of compounds (VIII), (IX) and (X) are in agreement with published data on indolizines and the structures of the compounds were determined by COSY, NOESY, HMQC and HMBC NMR experiments. Although pyridine is considered to be a weak nucleophile it can react with Michael-acceptors and the hypothetical compound (VIIb) could be a precursor of the indolizines. Compound (VIII) could then be formed after abstraction of 9-H of (VIIb), formation of a bond between C-4 and C-2' of the pyridyl residue, followed by hydrolysis of the enol ether and decarboxylation. The acetyl groups at C-3 of compounds (IX) and (X) are probably added during the reaction, as indolizines are known to be acetylated in this position by pyridine/acetic anhydride. However, the indolizine skeleton of compounds (IX) and (X) would appear to be formed after an attack by the cojugated enol of (VIIa) on C-2' of the pyridyl residue. In addition, a series of transformations including deacetylation and oxidation would have to take place, and the methyl group at C-1 in compounds (IX) and (X) would be the C-6 methyl group of papyracillic acid (I).

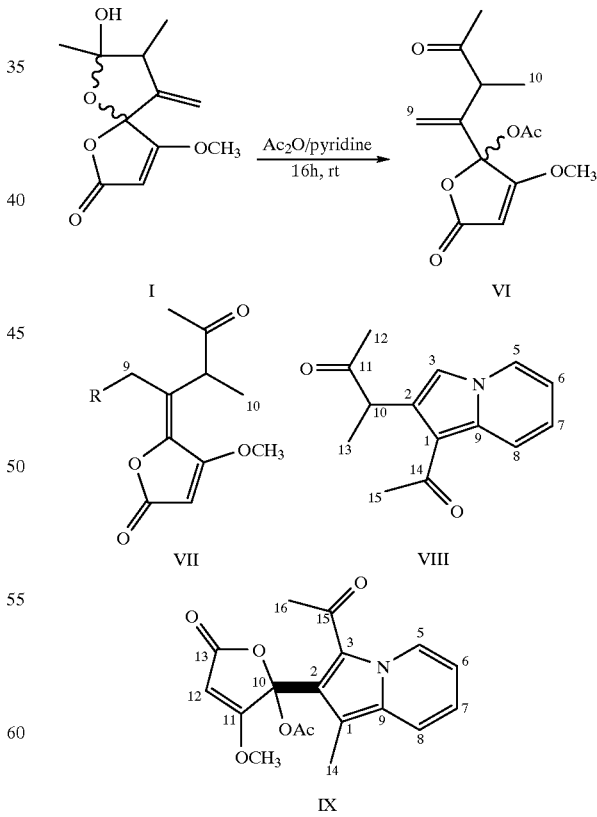

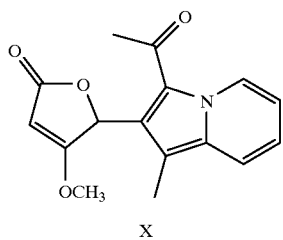

a: R = OAc; b: R = 1-pyridyl.

X

The proposed mechanism for the formation of VIII and IX is shown in the following scheme. As starting reaction the nucleophilic binding of the nucleophile at C-9 is suggested. In the case of the formation of VIII and IX the nucleophile is pyridine. The scheme illustrates two of the different reaction passes (I) can follow after initial nucleophilic binding of a nucleophile Y to C-9 of I.

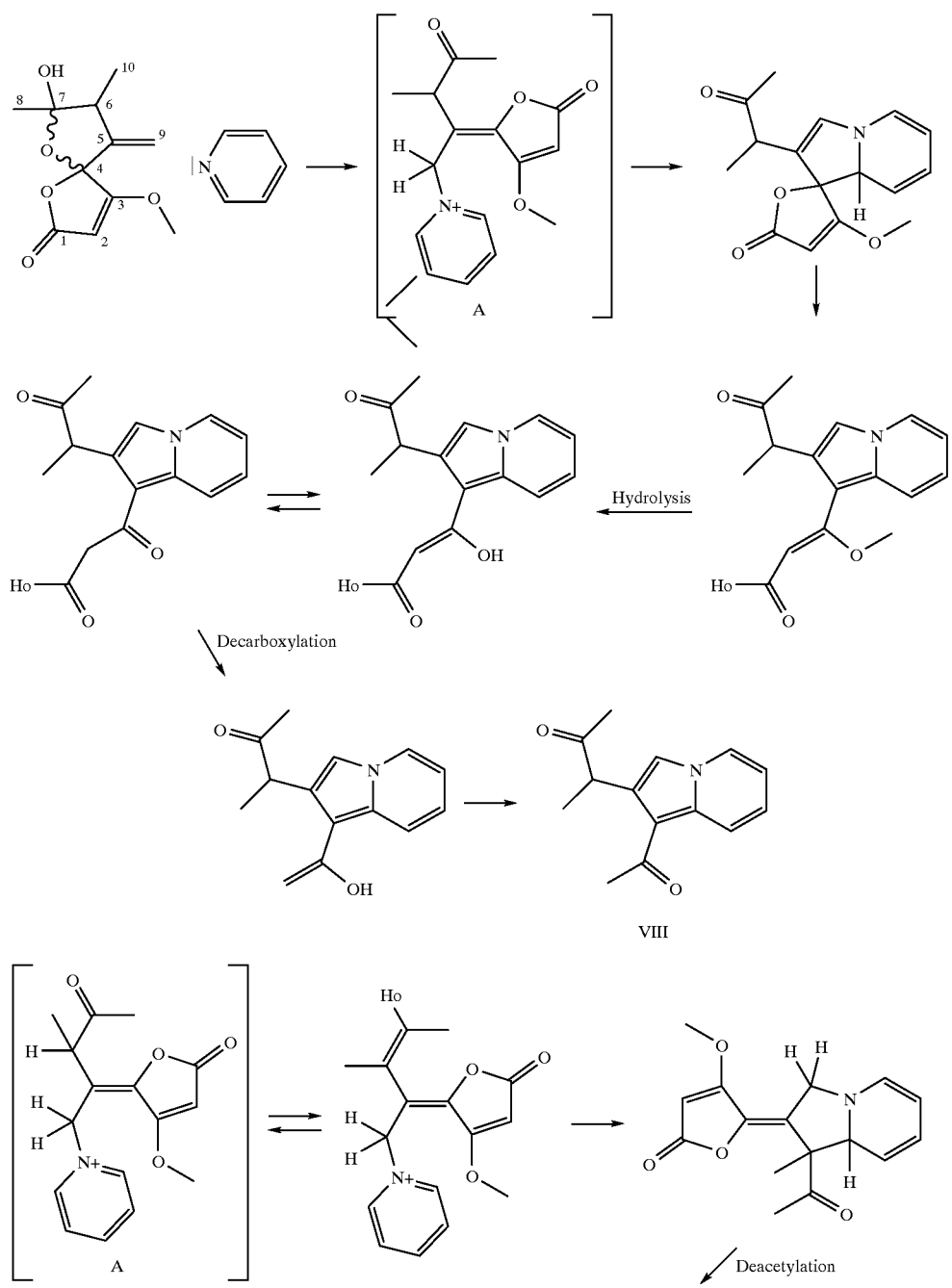

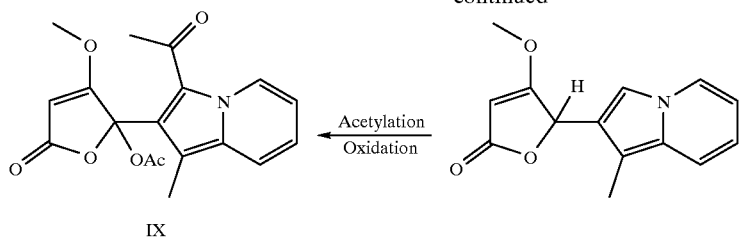

As an additional example, penicillic acid (II) was also acetylated, and the major products were isolated and characterised. The corresponding products were obtained, compound (XI) corresponds to compound (VI), (XII) is similar to (VIII) except that (XII) also was acetylated at C-3, and in (XIII) the C-3 acetyl group has (as the enol) been acetylated while the hydrolysis/decarboxylation has not taken place. (XIII) was obtained pure as the ethyl ester (XIIIb), formed during the evaporation of pyridine which was expedited by the addition of ethanol.

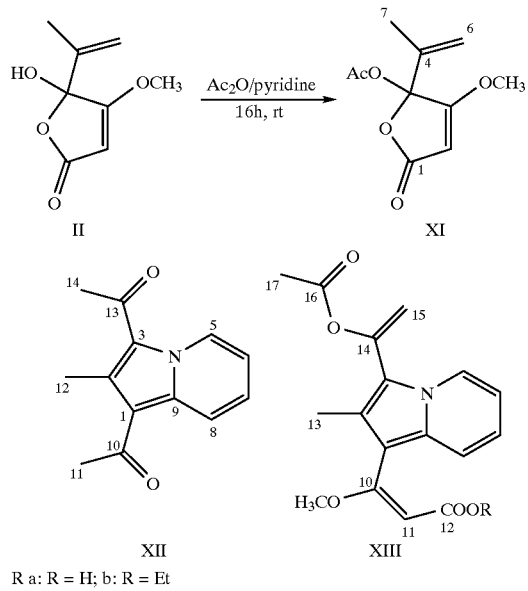

R a: R = H; b: R = Et

Preferred compound pluralities for search of lead structures and new drugs are obtained by reaction of I or II with heterocycles with nucleophilic activity more preferrable in addition to aceticanhydrid or chemical equivalents. Such libraries may have inter alia the following structure.

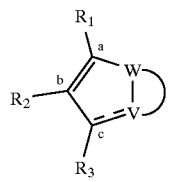

where W–V are part of heterocycle backbone, one W or V is preferrable, a heteroatom N, S or O and the other represents a C or CH.

a, b and c are part of the backbone of papyracillic or penicillic acid, where the carbons a, b, c are C-4, C-5 and C-6 of penicillic acid or a, b, c are C-4, C-5, C-9 of papyracillic acid respectively.

$R_1$, $R_2$ and $R_3$ represent either residues of papyracillic acid or residues formed by decarboxylation, acetylation, solvolysis etc. between the c-carbon and V is optionally a double bond.

Biological activity of papyracillic acid

Papyracillic acid and its derivatives show interesting pharmaceutical properties in different test systems. For example antibacterial activity ($\leq 10 \mu g/ml$) was found for (I) against *Bacillus brevis, Bacillus substilis, Micrococcus luteus* and *Enterobacter dissolvens*. Antifungal activity is observed with less or about 5 $\mu g/ml$ against *Nematosopra coryli*. It is less active (10 $\mu g/ml$) with *Mucor miehei, Penicillium notatum, Paecilomyces varioti*. The cytotoxic activity ($IC_{90}$) is determined to be in the range of 2–5 $\mu g/ml$.

The plate diffusion test was performed as described in "Biology of Antibioties", Springer Verlag, N.Y. 1972. The nutrient broth for bacteria was obtained from DIFCO. The growth medium for fungi and yeast contained 4 g yeastextract, 10 g Maltose, 4 g Glucose and 20 g Agar per 1 l water.

Biological activity of libraries with papyracillic acid as educt and deconvolution of libraries for identification of a single compound as drug or lead structure.

A compound plurality was obtained as given in example 8.

This compound plurality was active in assay (here fibrinogen-lowering assay). The compound plurality shows a fibrinogen synthesis inhibition of about 75% at 100 $\mu g/ml$. This compound plurality was deconvoluted into subsets by chromotographical extraction in 10 single compounds. One of them, compound (X), shows a very effective fibrinogen-lowering activity.

The test principle is the inhibition of fibrinogen synthesis in the human hepatoma cell line HepG2.

HepG2 cells were grown in culture flasks in MEM culture medium containing 10% fetal calf serum. $10^5$ cells/mi were seeded in 96-well-microtiter plates (Maxisorb®). The test substance was diluted in cell culture medium and added in increasing concentrations to the cells immediately after seeding. After a 48 hours' incubation period the supernatant is removed from the cells and the fibrinogen content was determined by ELISA. Plates were first coated overnight with 100 $\mu l$ of a monospecific polyclonal antibody directed against fibrinogen. After removing the excess antibody, the plates were washed three times with PBS/0.05% Tween®-20 and were subsequently incubated at room temperature for 1 hour in PBS/0.1% casein to block unspecific binding sites. After another wash 100 $\mu l$ aliquots of the appropriately diluted supernatant were added per well in triplicate and immunocomplexing as well as detection of the complexes formed were performed using a horseradish peroxidase (POD)-labelled monoclonal antibody directed against the E-domain of fibrin for immunodetection. ABTS® reduction catalyzed by POD was used for quantification, monitoring the absorbance at 405 nm by means of an ELISA reader.

Inhibition of fibrinogen synthesis was calculated as percentage of the fibrinogen content in the supernatant of wells containing untreated cells (controls) on the same microtiter plate.

| Control | Fibrinogen | 840 ng/ml | | | | |
|---|---|---|---|---|---|---|
| | Fibrinogen Synthesis Inhibition | | | | | |
| Compound (X) | 10 µg/ml | 3 µg/ml | 1 µg/ml | 0.3 µg/ml | 0.1 µg/ml | $IC^{50}$ µg/ml |
| | 77 | 30 | 10 | 6 | 1 | 5 |

Pharmaceutical compositions of papyracillic acid and its derivate. In order to produce pharmaceutical agents, the compounds of the general formula (I) or its derivates are mixed in a know manner with suitable pharmaceutical carrier substances, aromatics, flavourings and dyes and are formed for example into tablets or coated tablets or they are suspended or dissolved in water or an oil such as e.g. olive oil with addition of appropriate auxiliary substances.

The substance of the general formula (I) or its derivates can be administered orally or parenterally in a liquid or solid form. Water is preferably used as the injection medium which contains the stabilizing agents, solubilizers and/or buffers which ar usually used for injection solutions. Such additives are for example tartrate or borate buffers, ethanol, dimethylsulfoxide, complexing agents (such as ethylenediaminetetraacetic acid), high molecular polymers (such as liquid polyethylene oxide) for the regulation of the viscosity or polyethylene oxide) for the regulation of the viscosity or polyethylene derivatives of sorbitol anhydrides.

Solid carrier substances are e.g. starch, lactose, mannitol, methylcellulose, talcum, highly dispersed silicic acid, higher molecular fatty acids (such as stearic acid), gelatin, agar-agar, calcium phosphate, magnesium stearate, animal and vegetable fats or solid high molecular polymers (such as polyethylene glycols). Suitable formulations for the oral application can if desired contain flavourings and sweeteners.

The administered dose depends on the age, the health and the weight of the recipient, the extent of the disease, the type of treatments which are possibly being carried out concurrently, the frequency of the treatment and the type of the desired effect. The daily dose of the active compound is usually 0.1 to 50 mg/kg body weight.

Normally 0.5 to 40 and preferably 1.0 to 20 mg/kg/day in one or several applications per day are effective in order to obtain the desired results.

Structure of papyracillic acid and its derivatives

The structure determination of papyracillic acid (I) and its derivatives is based on 2D NMR experiments, and pertinent HMBC correlations. No molecular ion could, as expected, be observed in the EI or CI mass spectra of the two azo derivatives (IVa) and (IVb), however, by decreasing the temperature of the ion source from 250° C. to 110° C. the ion $M+NH_4^+$ (m/z 300) was approximately as abundant as the $M-N_2+NH_4^+$ (m/z 272) in the CI ($NH_3$) mass spectra of both compounds. In addition, the ions for $M_2+NH_4^+$ (m/z 582), $M_2-N_2+NH_4^+$ (m/z 554) and $M_2-N_4+NH_4^+$ (m/z 526) became stronger (3–5% of the base peak). The relative stereochemistry of (IVa) and (IVb) was suggested by the NOESY correlations observed and the chemical shifts of the C-6 methyl groups in the $^1H$ NMR spectrum. 10-$H_3$ correlate strongly to one of protons of C-9 and one of C-11 in both compounds, while 8-$H_3$ do not, suggesting that the C-6 methyl group is positioned above the five-membered ring in the most stable conformation of the two compounds. This is further supported by the weaker NOESY correlation observed between the C-3 methoxy protons and 6-H. The chemical shift for 10-$H_3$ is shifted upfield with 0.4 ppm in compound (IVa) compared to compound (IVb), and this could be explained by the stronger anisotropic effect of the azo function on 10-$H_3$ of compound (IVa).

The following examples are given for the purpose of illustrating this invention.

EXAMPLE 1

Strain A 48~88 of *Lachnum papyraceum* was maintained and cultivated on MGP medium (maltose 2%, glucose 1%, soypeptone 0.1%, yeast extract 0.1%, $KH_2PO_4$ 0.1%, $MgSO_4$ 0.005%, $CaCl_2$ $xH_2O$ 10 mM, $FeCl_3$ 6µM, $ZnSO_4$ $7H_2O$ 6 µM) and in the presence of 50–500 mM $CaBr_2$. Fermentations were carried out in a 20-liter fermentor (Braun Biostat U) at 24° C. with an aeration rate of 3.2 liters/minute and agitation (140 rpm). Oxygen saturation of the culture broth was measured using a Braun Oxygen electrode. Aliquots of the culture fluid (100 ml) were extracted twice with ethyl acetate. The combined extracts were dried with $Na_2SO_4$. An extract of *Lachnum papyraceum* was dissolved in methanol (50 ml), and subjected to flash chromatography on a silica gel column eluted with ethyl acetate/heptane 1:1. The fractions were analysed by TLC on silica gel plates in toluene:acetone 7:3, the Rf value of papyracillic acid in this system is 0.60 and upon spraying the plate with anisy aldehyde/sulfuric acid it gives a deep-green coloured spot. The fractions containing papyracillic acid were purified once more in the same system (silica gel column eluted with ethyl acetate: heptane 1:1) whereafter pure papyracillic acid was obtained from recrystallisation in methanol:water 1:5. The NMR spectra were recorded with a Bruker ARX500 spectrometer, the UV spectra with a Perkin Elmer λ16, the IR spectra with a Bruker IFS48, and the mass spectra with a Jeol SX102 spectrometer.

EXAMPLE 2

Papyracillic acid (I) was obtained as white crystals, m.p. 97–99° C. $[\alpha]_D$ 0° (c 1.0 in methanol). UV (methanol) $\lambda_{max}$ (ε): 226 nm (6,200). IR (KBr): 3450, 2920, 1770, 1640, 1360, 1210, 940 and 860 cm$^{-1}$. $^1H$ NMR (500 MHz in $CDCl_3$), δ, mult. J (Hz): 5.23–5.05, 2-H and 9-$H_2$; 3.89, 3.85, 3.84 and 3.83, 4s, 3-$OCH_3$; 2.89, dm, $J_{6-10}$=7.2; 2.84, 2.75 and 2.66, ddq, $J_{6-9a}$=3, $J_{6-9b}$=3, $J_{6-10}$=7, 6-H; 1.57, 1.54, 1.38 and 1.36, 4s, 8-$H_3$; 1.14, 1.13, 1.13 and 1.10, 4d, $J_{6-10}$=7, 10-$H_3$. $^{13}C$ NMR (125 MHz in $CDCl_3$), δ: 178.2, 177.9, 176.7 and 176.2 C-3; 170.4, 170.3, 170.2 C-; 149.4, 148.3, 148.2 and 147.8 C-5; 111.4, 111.3, 111.2 and 110.9 C-9, 109.5, 109.2, 107.3 and 107.3 C-7; 107.3, 107.3, 107.1 and 106.2 C-4; 91.1, 90.2, 88.8, 88.4 C-2; 60.1, 60.0, 60.0, 59.8 OCH3; 47.9, 47.4, 47.0 and 45.1 C-6, 25.1, 24.4, 22.6 and 22.4 C-8; 15.2, 12.7, 10.9 and 10.4 C-10. MS (EI, 70 eV), m/z: 209.0791 (M$^+$-OH, 100%, $C_{11}H_{13}O_4$ requires 209.0814), 184 (12%), 166 (56%), 139 (29%), 123 (13%), 69 (18%), 43 (24%).

EXAMPLE 3

The reaction of I yielding Acetals is performed in a usual manner by katalyzing with acid. The methylated compound of (I) ($OCH_3$ @ C-7 of (I)) was obtained by stirring at room temperature leaving Papyracillic acid (I) in Methanol with traces of trifluoracetic acid present.

A mixture of isomers was obtained, from which the methylated compound could be isolated as the major isomer. White crystals, m.p. 116–118° C. $[\alpha]_D$ 42° (c 1.3 in methanol). UV (methanol) $\lambda_{max}$ ($\epsilon$): 224 nm (9,800). IR (KBr): 2940, 1770, 1640, 1460, 1360, 1210, 950 and 870 cm$^{-1}$. $^1$H NMR (500 MHz in CDCl$_3$), δ, mult. J (Hz): 5.12, d, $J_{6-9a}$=3, 9-HA; 5.10, d, $J_{6-9b}$=3, 9-Hb; 5.01, s, 2-H; 3.81, s, 3-OCH3; 3.23, s, 7-OCH3; ddq, $J_{6-9a}$=3, $J_{6-9b}$=3, J-10= 6.8, 6-H; 1.43, s, 8-H3, 1.08, d, J6–10=6.8, 10-H$_3$. $^{13}$C NMR (125 MHz in CDCl$_3$), δ: 178.0 C-3; 170.1 C-1; 148.5 C-5; 109.6 C-9; 109.1 C-7; 106.8 C-4; 88.1 C-2; 59.6 3-OCH3; 49.2 7-OCH3; 48.5 C-6; 18.7 C-8; 10.3 C-10. MS (EI, 70 eV), m/z: 209.0788 (M+-OCH3, 54%, C11H1304 requires 209.0814), 166 (100%), 151 (29%), 123 (31%), 69 (39%), 43 (43%).

EXAMPLE 4

Methyl papyracillate (M) was obtained as a colourless oil. $[\alpha]_D$ +25° (c 1.0 in chloroform). UV (methanol) $\lambda_{max}$ ($\epsilon$): 224 nm (11,700). IR (KBr): 2950, 1715, 1685, 1620, 1370, 1195, 1145 and 1020 cm$^{-1}$. $^1$H NMR (500 MHz in CDCl$_3$), δ, mult. J(Hz): 6.00 and 5.95, 2s, 9-H$_2$; 5.23, s, 2-H; 3.82, q, $J_{6-10}$=7.2, 6-H; 3.70, s, 3-OCH$_3$; 3.56, s, 1-OCH$_3$; 2.15, s, 8-H$_3$; 1.19, d, $J_{6-10}$=7.2, 10-H$_3$. $^{13}$C NMR (125 MHz in CDCl$_3$), δ: 207.8 C-7; 191.0 C-4; 167.2 C-3, 166.2 C-1; 146.1 C-5; 129.2 C-9; 93.1 C-2; 56.8 3-OCH$_3$; 51.1 1-OCH$_3$; 45.4 C-6; 28.4 C-8; 15.1 C-10. MS (EI, 70 eV), m/z: 240.0976 (M$^+$, 20%, C$_{15}$H$_{22}$O$_2$ requires 240.0998), 208 (42%), 198 (99%), 166 (60%), 139 (100%), 123 (29%), 69 (42%), 43 (73%).

EXAMPLE 5

Compound (IVa) was obteines as white crystals, m.p. 97–99° C., in 10% yield after methylation of papyracillic acid (I) with TMS-diazomethane in methanol: benzene 1:1 at room temperature for 5 h. $[\alpha]_D$ +34° (c 0.6 in chloroform). UV (methanol) $\lambda_{max}$ ($\epsilon$): 222 nm (7,800). IR (KBr): 2920, 1710, 1700, 1620, 1445, 1360, 1200, 1140, 1070 and 815 cm$^{-1}$. $^1$H NMR(500MHz in CDCl$_3$), δ, mult. J(Hz): 5.14, s, 2-H; 4.66, ddd, $J_{9a-11a}$=6.4, $J_{9b-11a}$=10.2, $J_{11a-11b}$=18.2, 11-Ha; 4.56, ddd, $J_{9a-11b}$=9.9, $J_{9b-11b}$=5.7, $J_{11a-11b}$=18.2, 11-Hb, 4.01, q, $J_{6-10}$=7.0, 6-H; 3.80, s, 3-OCH3; 3.57, s, 1-OCH3, 2.23, s, 8-H3, 2.12, ddd, $J_{9a-9b}$=13.9, $J_{9a-11a}$=6.4, $J_{9a-11b}$=9.9, 9-Ha, 2.04, ddd, $J_{9a-9b}$=13.9, $J_{9b-11a}$=10.1, $J_{9b-11b}$=5.7; 0.79, d, $J_{6-10}$=7.0, 10-H3. 13C NMR (125 Mhz in CDCL3), :208. C-7; 197.7 C-4; 167.5 C-3; 166.9 C-1, 105.2, C-5; 93.0 C-2; 79.1 C-11; 57.4 3-OCH3, 51.6 1-OCH3, 47.3 C-6; 31.2 C-8; 20.3 C-9; 11.2 C-10. MS (EI, 79 eV), m/z: 254.1137 (m$^+$–N2, 5%, C13H18O5 requires 254.1154), 222 (8%), 212 (32%), 211 (19%), 179 (17%), 153 (100%), 137 (18%), 111 (21%), 69 (26%), 43 (50%). MS (CI, nH3, ion source temperature 20° C.), m/z: 272 (m–N2+NH4+, 82%), 255 (m–N2+H+, 13%), 237 (32%).

EXAMPLE 6

Compound (IVb) was obtained as a colourness oil in 10% yield after methylation of papyracillic acid (I) (vide supra). $[\alpha]_D$ +10° (c 0.5 in chloroform). UV (methanol) $\lambda_{max}$ ($\epsilon$): 222 mn (8,400). IR (KBr): 2920, 1700, 1615, 1435, 1360, 1190 and 1140 cm$^{-1}$. $^1$H NMR (500 MHz in CDCl$_3$), δ, mult. J(Hz): 5.15, s, 2-H; 4.66, ddd, $J_{9a-11a}$=6.3, $J_{9b-11a}$=8.5, $J_{11a-11b}$=18.1, 11-Ha; 4.63, ddd, $J_{9a-11b}$=7.9, $J_{9b-11b}$=7.0, $J_{11a-11b}$=18.1, 11-Hb, 4.03, q, $J_{6-10}$=7.2, 6-H; 3.84, s, 3OCH3; 3.55, s, 1-OCH3; 2.13, s, 8-H3, 2.07, ddd, $J_{9a-9b}$=12.7, d, $J_{9b-11a}$=8.5, $J_{9b-11b}$=7.0, 1.17, d, $J_{6-10}$=7.2, 10-H3 13C NMR data were not recorded. MS (EI, 70 eV), m/z: 254.1159 (m$^+$–N2, 7%, C13H18O5 requires 254.1154), 223 (12%), 212 (38&), 211 (59%), 179 (30%), 153 (100%), 137 (28%), 111 (37%), 69 (38%), 43 (72%). MS (CI, NH3, ion source temperature 250° C.), m/z: 272 (m–N2+NH4+, 100%), 255 (M–N2+H+, 27%), 237 (34%). MS (CI, NH3, ion source temperature 110° C.), m/z: 300 (M+NH4+, 100%), 272 (M–N2+NH4+, 85%), 255 (m–N2+H+, 8%), 237 (23%).

EXAMPLE 7

The compounds (V) were obtained as a mixture (library) or as single compounds as follows:

Compound (Va) was obtained as yellowish oil in 42% yield after the reaction between papyracillic acid (I) (29 mg, 0.13 nmol) and cysteine (29 mg, 0.12 nmol) in 1 ml Phosphatpuffer pH7, 0.1M at 37° C. for 15 mins and purification by reversed phase HPLC (O to 30% methanol in water during 60 min) and repeated silica gel chromatography (MTBE:MeOH 8:1). $[\alpha]_D$-125° (c 1.0 in methanol). UV (methanol) $\lambda_{max}$ ($\epsilon$): 224 nm (6,400). IR (KBr): 3420, 1750, 1640, 1390 and 870 cm$^{-1}$. $^1$H NMR, 500 MHz in CD$_3$OD (δ, mult., J): 5.26, s, 2-H; 3.96, s, 3-OCH$_3$; 3.70, dd, $J_{11a-12}$=3.6, $J_{11b-12}$=8.8, 12-H; 3.13, dd, $J_{11a-11b}$=14.6, $J_{11a-12}$=3.6, 11-Ha; 2.87, dd, $J_{11a-11b}$=14.6, $J_{11b-12}$=8.8, 11-Hb; 2.83, dd, $J_{5-9a}$=3.8, $J_{9a-9b}$=13.5, 9-Ha, 2.74, m, 5-H, 2.59, dd, $J_{5-9b}$=10.2, $J_{9a-9b}$=13.5, 9-Hb; 2.03, dq, $J_{5-6}$ 32 11.5, $J_{6-10}$=6.7, 6-H; 1.47, s, 8-H$_3$; 1.11, d, $J_{6-10}$=6.7, 10-H$_3$. 13C NMR, 125 MHz in CD$_3$OD (δ): 180.1 C-3; 172.8 and 172.7 C-1 and C-13; 110.0 C-4, 108.8 C-7, 91.3 C-2; 60.7 3-OCH$_3$; 54.8 C-12; 49.1 C-5; 47.6 C-6; 34.7 C-11; 29.8 C-9; 26.6 C-8; 12.2 C-10. MS (FAB positive ions), m/z: 370 (M+Na$^+$) and 348 (M+H$^+$).

The cysteine methyl ester adduct Compound (Vb) was obtained as a yellow oil in 52% yield after the reaction between papyracillic acid (I) (29 mg, 0.13 mmol) and cysteine methyl ester (21 mg, 0.12 mmol) in 1 ml Phosphatpuffer pH7, 0.1M at 37° C. for 15 mins and purification by reversed phase HPLC (O to 30% methanol in water during 60 min) and repeated silica gel chromatography (MTBE:MeOH 8:1). $[\alpha]_D$ –106° (c 1.0 in methanol). UV (methanol) $\lambda_{max}$ ($\epsilon$): 222 nm (8,200). IR (KBr): 3400, 2950, 1750, 1640, 1450, 1380, 1220, 1020 and 870 cm$^{-1}$. $^1$H NMR, 500 MHz in CDCl$_3$ (δ, mult., J): 5.07, s, 2-H; 3.90, s, 3-OCH$_3$; 3.70, s, 13-OCH$_3$; 3.60, dd, $J_{11a-12}$=4.7, $J_{11b-12}$=7.2, 12-H; 2.83, dd, $J_{11a-11b}$=13.5, $J_{11a-12}$=4.7, 11-Ha; 2.70, dd, $J_{11a-11b}$=13.5, $J_{11b-12}$=7.2, 11-Hb; 2.67–2.52, m, 9-Ha, 5-H and 9-Hb; 2.00, dq, $J_{5-6}$=11.5, $J_{6-10}$=6.7, 6-H; 1.49, s, 8-H$_3$; 1.08, d, $J_{6-10}$=6.7, 10-H$_3$. $^{13}$C NMR, 125 MHz in CDCl$_3$ (δ): 177.1 C-3; 174.1 C-13; 169.6 C-1; 108.1 C4; 107.2 C-7; 90.4 C-2; 59.7 3-OCH$_3$; 53.6 C-12; 52.3 13-OCH$_3$; 48.2 C-5; 46.0 C-6; 37.8 C-11, 29.5 C-9; 26.2 C-8; 11.7 C-10. MS (FAB, positive ions) m/z: 362 (M+H$^+$).

EXAMPLE 8

Compounds (VI)–(X) were obtained after the treatment of papyracillic acid (I) with acetic anhydride:pyridine (1:5) at room temperature for 16 hours. The yields after separation were 63% of (VI), 9% of (VII), 5% of compound (VIII), 3% of (IX), and 7% of (X).

Compound (VI), 5-Acetoxy4-methoxy-5-(1-(1-methyl-2-oxopropyl)vinyl)-2,5-dihydro-2-furanone was obtained as white crystals, m.p. 55–57° C., as a 3:2 epimeric mixture. $[\alpha]_D$ +25° (c 1.1 in chloroform). UV (methanol) $\lambda_{max}$ ($\epsilon$): 230 nm (7,400). IR (KBr): 1776, 1716, 1343, 1197, 1178, 1070 and 1028 cm$^{-1}$. $^1$H NMR, 500 MHz in CDCl$_3$ (δ, mult., J): 5.55 and 5.21, m, 9-H$_2$; 5.20 and 5.13, s, 3-H; 3.85 and 3.87, s, 2-OCH$_3$; 3.27 and 3.43, q, $J_{6-10}$=7.0, 6-H; 2.10 and 2.06, s, 8-H$_3$; 2.04 and 2.01, s, 4-OAc; 1.12 and 1.19, d, $J_{6-10}$=7.0, 10-H$_3$. $^{13}$C NMR, 125 MHz in CDCl$_3$ (δ): 207.1 and 207.6 C-7; 177.1 and 177.7 C-2; 168.2 and 168.2 C-1; 167.2 and 167.2 4-OAc; 142.2 and 142.7 C-5; 117.7 and 117.4 C-9; 101.0 and 100.9 C-4; 90.5 and 89.8 C-3; 59.8 and 59.9 2-CH$_3$; 46.5 and 47.7 C-6; 27.7 and 27.3 C-8; 21.1 and 21.1 4-OAc; 17.1 and 16.5 C-10. MS (EI, 70 eV), m/z: 226.0860 (M$^+$-CH$_2$CO, 12%, C$_{11}$H$_{14}$O$_5$ requires 226.0841), 209 (6%), 208 (6 %), 166 (100%), 151 (14%), 139 (25%), 123 (21%). MS (CI, NH$_3$), m/z: 286 (M+NH$_4^+$, 100%).

Compound (VIIa), 5-(1-Acetoxymetyl-2-methyl-3-oxo-(Z)-butylidene)-4-methoxy-2,5-dihydro-2-furanone was obtained as white crystals, m.p. 54–56° C. [α]$_D$ +250° (c 1.1 in chloroform). UV (methanol) λ$_{max}$ (ε): 263 nm (11,400). IR (KBr): 1782, 1745, 1717, 1607, 1441, 1366, 1229, 1027 and 970 cm$^{-1}$. $^1$H NMR, 500 MHz in CDCl$_3$ (δ, mult., J): 5.38, s, 2-H; 5.10, d, J$_{9a-9b}$=12.9, 9-Ha; 4.86, d, J$_{9a-9b}$=12.9, 9-Hb; 3.94, s, 2-OCH$_3$; 3.93, q, J$_{6-10}$=7.0, 6-H; 2.13, s, 8-H$_3$; 1.97, s, 4-OAc; 1.22, d, J$_{6-10}$=7.0, 10-H$_3$. $^{13}$C NMR, 125 MHz in CDCl$_3$ (δ): 206.0 C-7; 170.4 4-OAc; 170.1 C-2; 166.6 C-1, 143.1 C-4; 120.3 C-5; 92.0 C-3; 59.7 2-CH$_3$; 58.2 C-9; 47.6 C-6; 28.3 C-8; 20.5 4-OAc; 12.9 C-10. MS (EI, 70 eV), m/z: 268 (M$^+$, 2%), 226.0852 (M$^+$- CH$_2$CO, 33%, C$_{11}$H$_{14}$O$_5$ requires 226.0841), 209 (3%), 166 (100%), 151 (11%), 137 (14%), 123 (16%). MS (CI, NH$_3$) m/z: 286 (M+NH$_4^+$, 100%).

Compound (VIII), 1-Acetyl-2-(1-methyl-2-oxo-propyl)-indolizine was obtained as a greenish oil. [α]$_D$ +428° (c 1.2 in chloroform). UV (methanol) λ$_{max}$ (ε): 233 nm (20,200), 271 nm (4,000), 280 nm (4,000), 350 nm (11,900). IR (KBr): 1711, 1622, 1501, 1426, 1352, 1238, 1158 and 963 cm$^{-1}$. $^1$H NMR, 500 MHz in CDCl$_3$ (δ, mult., J): 7.97, d, J$_{5-6}$=6.8, 5-H; 7.84, d, J$_{7-8}$=9.2, 8-H; 7.18, d, J$_{3-10}$=0.8, 3-H; 7.08, dd, J$_{6-7}$=7, J$_{7-8}$=9, 7-H; 6.71, dd, J$_{5-6}$J$_{6-7}$=7, 6-H; 4.62, dd, J$_{3-10}$=0.8, J$_{10-13}$=7.2, 10-H, 2.61, s, 15-H$_3$; 2.31, s, 12-H$_3$; 1.47, d, J$_{10-13}$=7.2, 13-H$_3$. $^{13}$C NMR, 125 MHz in CDCl$_3$ (δ): 209.9 C-11; 192.0 C-14; 136.3 C-9; 132.1 C-2; 126.4 C-5; 123.4 C-7; 119.0 C-8; 114.1 C-3, 112.2 C-6; 112.2 C-1; 45.0 C-10; 31.0 C-14; 28.8 C-12; 16.4 C-13. MS (EI, 70 eV), m/z: 229.1105 (M$^+$, 87%, C$_{14}$H$_{15}$O$_2$N requires 229.1103), 214 (10%), 212 (8%), 186 (100%), 172 (65%), 170 (28%), 144 (79%), 143 (39%). MS (CI, NH$_3$), m/z: 230 (M+H$^+$, 100%).

Compound (IX), 5-(3-Acetyl-1-methyl-2-indolizinyl)-5-acetoxy-4-methoxy-2,5-dihydro-2-furanone was obtained as a greenish oil. [α]$_D$ +84° (c 0.4 in chloroform). UV (methanol) λ$_{max}$ (ε): 231 nm (28,400), 377 nm (6,700). IR (KBr): 1775, 1648, 1453, 1370, 1339, 1198, 1159 and 1013 cm$^{-1}$. $^1$H NMR, 500 MHz in CDCl$_3$ (δ, mult., J): 8.95, d, J$_{5-6}$=7.3, 5-H; 7.43, d, J$_{7-8}$=9.0, 8-H; 6.94, dd, J$_{6-7}$=6.5, J$_{7-8}$=9.0, 7-H; 6.71, dd, J$_{5-6}$=J$_{6-7}$=7, 6-H; 5.33, s, 12-H; 3.94, s, 11-OCH3; 2.69, s, 16-CH3; 2.31, s, 14-H$_3$; 2.14, s, 10-OAc. $^{13}$C NMR, 125 MHz in CDCl$_3$ (δ): 192.9 C-15; 177.8 C-11; 168.4 C-13; 167.4 10-OAc; 133.6 C-9; 126.1 C-5; 122.7 C-2; 122.4 C-3; 121.1 C-7; 117.2 C-8; 113.8 C-6; 109.1 C-1; 101.0 C-10; 90.6 C-12; 60.0 11-OCH$_3$; 31.9 C-16; 21.5 10-OAc; 9.8 C-14. MS (EI, 70 eV), m/z: 343.1059 (M$^+$, 88%, C$_{18}$H$_{17}$O$_6$N requires 343.1056), 300 (8%), 283 (20%), 258 (79%), 242 (100%), 200 (45%). MS (CI, NH$_3$), m/z: 344 (M+H$^+$, 59%), 284 (100%).

Compound (X), 5-(3-Acetyl- 1-methyl-2-indolizinyl)-4-methoxy-2,5-dihydro-2-furanone was obtained as a greenish oil. [α]$_D$ +239° (c 1.5 in chloroform). UV (methanol) λ$_{max}$ (ε): 230 nm (17,400), 259 nm (7,900), 378 nm (4,800). IR (KBr): 1754, 1632, 1458, 1375, 1235 and 1158 cm$^{-1}$. $^1$H NMR, 500 MHz in CDCl$_3$ (δ, mult., J): 9.81, d, J$_{5-6}$=7.3, 5-H; 7.47, d, J$_{7-8}$=8.8, 8-H; 7.11, dd, J$_{6-7}$=7.7, J$_{7-8}$=8.8, 7-H; 6.84, dd, J$_{5-6}$=J$_{6-7}$=7, 6-H; 6.66, d, J$_{10-12}$=1.3, 10-H; 5.31, d, J$_{10-12}$=1.3, 12-H; 3.90, s, 11-OCH$_3$; 2.68, s, 16-CH$_3$; 2.21, s, 14-CH$_3$. $^{13}$C NMR, 125 MHz in CDCl$_3$ (δ): 186.3 C-15; 180.3 C-11; 172.1 C-13, 136.2 C-9; 128.3 C-5; 124.2 C-2; 123.3 C-7; 122.1 C-3; 116.5 C-8; 114.4 C-6; 111.2 C-1; 89.4 C-12; 74.8 C-10; 59.8 11-OCH$_3$; 31.2 C-16; 8.8 C-14. MS (EI, 70 eV), m/z: 285.1009 (M$^+$, 65%, C$_{16}$H$_{15}$O$_4$N requires 285.1001), 259 (11%), 243 (100%), 242 (70%), 228 (48%), 200 (17%), 158 (14%), 154 (15%), 130 (20%). MS (CI, NH$_3$), m/z: 303 (M+NH$_4^+$, 15%), 284 (M+H$^+$, 100%).

EXAMPLE 9

Compounds (XI)–(XIII) were obtained after the treatment of penicillic acid (II) with acetic anhydride:pyridine (1:5) at room temperature for 16 hours. The yields after separation were 58% of (XI), 2% of (XII) and 5% of (XIII).

Compound (XI), 5-Acetoxy-5-(1-methyl-1-ethenyl)-4-methoxy-2,5-dihydro-2-furanone was obtained as white crystals, m.p. 72–74° C. UV (methanol) λ$_{max}$ (ε): 230 nm (10,100). IR (KBr): 3125, 1765, 1640, 1460, 1370, 1350, 1270, 1225, 1200, 1120, 1100, 1030, 950, 910, 840 and 800 cm$^{-1}$. $^1$H NMR, 500 MHz in CDCl$_3$ (δ, mult., J): 5.34, m, 6-Ha; 5.15, s, 2-H; 5.13, m, 6-Hb; 3.88, s, 3-OCH$_3$; 2.08, s, 4-OAc; 1.79, m, 7-H$_3$. $^{13}$C NMR, 125 MHz in CDCl$_3$ (δ): 178.0 C-3; 169.0 C-1; 167.7 4-OAc; 138.3 C-5; 116.0 C-6; 101.3 C-4, 89.7 C-2; 59.9 3-OCH$_3$; 21.3 4-OAc; 17.3 C-7. MS (EI, 70 eV), m/z: 212.0662 (M$^+$, 42%, C$_{10}$H$_{12}$O$_5$ requires 212.0685), 169 (61%), 152 (39%), 142 (27%), 126 (39%), 124 (28%), 100 (94%), 68 (84%), 43 (100%).

Compound (XII), 1,3-Diacetyl-2-methylindolizine was obtained as yellow oil. UV (methanol) λ$_{max}$ (ε): 234 nm (8,300), 260 (8,600), 290 (5,100), 336 (6,400) and 348 (6,600). IR (KBr): 2920, 1770, 1640, 1610, 1490, 1410, 1390, 1200 and 910 cm$^{-1}$. $^1$H NMR, 500 MHz in CDCl$_3$ (δ, mult., J): 10.00, d, J$_{5-6}$=7.1, 5-H; 8.30, d, J$_{7-8}$=9.0, 8-H; 7.38, dd, J$_{6-7}$=6.8, J$_{7-8}$=9.0, 8-H; 6.97, dd, J$_{5-6}$=J$_{6-7}$=7, 6-H; 2.87, s, 12-H$_3$; 2.65, s, 11-H$_3$; 2.65, s, 14-H$_3$. $^{13}$C NMR, 125 MHz in CDCl$_3$ (δ): 192.8 C-13; 189.1 C-10; 138.5 C-9; 135.3 C-2; 128.9 C-5; 127.8 C-7, 123.2 C-3; 118.7 C-8; 115.5 C-1; 114.8 C-6; 31.9 C-14; 31.6 C-11; 14.9 C-12. MS (EI, 70 eV), m/z: 215.0954 (M$^+$, 39%, C$_{13}$H$_{13}$NO$_2$ requires 215.0946), 200 (100%), 186 (6%), 172 (10%), 158 (11%), 143 (8%), 130 (15%), 43 (13%).

Compound (XIII), 3-(3-(1-Acetoxy-1-ethenyl)-2-methyl-1-indolizinyl)-3-methoxy-(E)-2-propenoic acid ethyl ester was obtained as a yellow oil. UV (methanol) λ$_{max}$ (ε): 230 nm (21,100), 260 (15,000), 330 (8,700) and 352 (8,700). IR (KBr): 2975, 2930, 1760, 1710, 1605, 1520, 1490, 1370, 1195, 1140, 1125, 1100 and 1050 cm$^{-1}$. $^1$H NMR, 500 MHz in CDCl$_3$ (δ, mult., J): 8.12, d, J$_{5-6}$=7.1, 5-H; 7.24, d, J$_{7-8}$=9.0, 8-H; 6.81, dd, J$_{6-7}$=6.6, J$_{7-8}$=9.0, 7-H; 6.55, dd, J$_{5-6}$=J$_{6-7}$=7, 6-H; 5.41, d, J$_{15a-15b}$=1.5, 15-Ha; 5.40, s, 11-H; 5.21, d, J$_{15a-15b}$=1.5, 15-Hb; 4.01, q, J=7.1, 12-OC$\underline{H}_2$CH$_3$; 3.82, s, 10-OCH$_3$, 2.28, s, 13-H3; 2.11, s, 17-H$_3$; 1.08, t, J=7.1, 12-OCH$_2$C$\underline{H}_3$. $^{13}$C NMR, 125 MHz in CDCl$_3$ (δ): 168.8 C-16; 166.8 C-12; 166.0 C-10; 144.6 C-14; 132.6 C-9; 126.2 C-2, 124.2 C-5; 119.8 C-7; 118.0 C-8; 117.8 C-3; 111.1 C-6; 109.0 C-15; 107.7 C-1; 93.5 C-11; 59.4 12-O$\underline{C}$H$_2$CH$_3$; 55.9 10-OCH$_3$; 20.8 C-17; 14.2 12-OCH$_2$$\underline{C}$H$_3$; 11.1 C-13. MS (EI, 70 eV), m/z: 343.1431 (M$^+$, 100%, C$_{19}$H$_{21}$NO$_5$ requires 343.1420), 314 (22%), 300 (47%), 286 (46 %), 284 (52%), 272 (45%), 256 (32%), 240 (29%), 228 (22%), 212 (41%), 198 (50%), 182 (33%), 168 (26%), 154 (30%).

We claim:

1. A compound of formula (I)

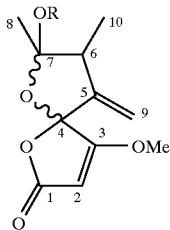

wherein R is hydrogen or a branched or unbranched $C_1$–$C_4$ alkyl, or a tautomer, enantiomer or pharmaceutically acceptable salt thereof.

2. A process for producing the compound as claimed in claim 1, the process comprising culturing a strain of the class Ascomycetes which is capable of producing the copound in a nutrient medium containing $CaBr_2$.

3. The process as claimed in claim 2, wherein the strain is of species *Lachnum papyraceum.*

4. The process as claimed in claim 2, wherein the strain is of *Lachnum papyraceum,* strain 48–88.

5. A process for producing a plurality of compounds, comprising reacting the compound as claimed in claim 1 with at least one nucleophile independently selected from the group consisting of an amine of an aliphatic or aromatic hydrocarbon, an alcohol of an aliphatic or aromatic hydrocarbon, a thiol of an aliphatic or aromatic hydrocarbon and a heterocycle.

6. A plurality of compounds obtainable by the process as claimed in claim 5.

7. The process as claimed in claim 5, further comprising separating a portion of the plurality of compounds into at least one subgroup.

8. The process as claimed in claim 5, wherein the at least one nucleophile reacts with the carbon at position 9 of the compound.

9. The process as claimed in claim 5, further comprising isolating at least one compound individually from the plurality of compounds.

10. A compound obtainable by the process as claimed in claim 9.

11. A process for producing a compound, comprising reacting the compound as claimed in claim 1 with a nucleophile selected from the group consisting of an amine of an aliphatic or aromatic hydrocarbon, an alcohol of an aliphatic or aromatic hydrocarbon, a thiol of an aliphatic or aromatic hydrocarbon and a heterocycle.

12. A compound obtainable by the process as claimed in claim 11.

13. The process as claimed in claim 11, wherein the nucleophile reacts with the carbon at position 9 of the compound.

14. A process for determining the presence or absence of any interaction between a compound and a pharmaceutical target of interest, the process comprising
    (a) providing a pharmaceutical target of interest;
    (b) incubating the target with the plurality of compounds as claimed in claim 6, and
    (c) determining the presence or absence of any interaction between the plurality of compounds and the target.

15. A process for determining the presence or absence of any interaction between a compound and a pharmaceutical target of interest, the process comprising
    (a) providing a pharmaceutical target of interest;
    (b) incubating the target with the compound as claimed in claim 10, and
    (c) determining the presence or absence of any interaction between the at least one compound and the target.

16. A process for determining the presence or absence of any interaction between a compound and a pharmaceutical target of interest, the process comprising
    (a) providing a pharmaceutical target of interest;
    (b) incubating the target with the compound as claimed in claim 12, and
    (c) determining the presence or absence of any interaction between the at least one compound and the target.

17. The process as claimed in claim 14, wherein the target is selected from the group consisting of a protein, a cell or cell part, DNA and RNA.

18. The process as claimed in claim 15, wherein the target is selected from the group consisting of a protein, a cell or cell part, DNA and RNA.

19. The process as claimed in claim 16, wherein the target is selected from the group consisting of a protein, a cell or cell part, DNA and RNA.

20. A pharmaceutical composition suitable for treating a bacterial or fungal infection, comprising the compound as claimed in claim 1 and a pharmaceutically acceptable carrier.

21. A pharmaceutical composition suitable for treating a bacterial or fungal infection, comprising at least one of the plurality of compounds as claimed in claim 6 and a pharmaceutically acceptable carrier.

22. A pharmaceutical composition suitable for treating a bacterial or fungal infection, comprising the compound as claimed in claim 10 and a pharmaceutically acceptable carrier.

23. A pharmaceutical composition suitable for treating a bacterial or fungal infection, comprising the compound as claimed in claim 12 and a pharmaceutically acceptable carrier.

* * * * *